United States Patent [19]

Feldman et al.

[11] Patent Number: 5,399,866
[45] Date of Patent: Mar. 21, 1995

[54] OPTICAL SYSTEM FOR DETECTION OF SIGNAL IN FLUORESCENT IMMUNOASSAY

[75] Inventors: Sandra F. Feldman, Schenectady; Carl M. Penney, Saratoga Springs, both of N.Y.

[73] Assignee: General Electric Company, Schenectady, N.Y.

[21] Appl. No.: 36,573

[22] Filed: Mar. 24, 1993

[51] Int. Cl.[6] .......................................... G01N 21/64
[52] U.S. Cl. .................... 250/458.1; 356/318
[58] Field of Search ................ 356/317, 417, 318; 250/458.1, 459.1, 461.1

[56] References Cited

U.S. PATENT DOCUMENTS

| | | | |
|---|---|---|---|
| 4,368,047 | 1/1983 | Andrade et al. | 435/4 |
| 4,533,246 | 8/1985 | Braum | 356/317 |
| 4,582,809 | 4/1986 | Block et al. | 436/527 |
| 4,585,344 | 4/1986 | Webster | 356/318 |
| 4,648,892 | 3/1987 | Kittrell et al. | 65/4.21 |
| 4,654,532 | 3/1987 | Hirshfield | 250/458.1 |
| 4,852,967 | 8/1989 | Cook et al. | 350/96.29 |
| 4,929,561 | 5/1990 | Hirschfeld | 250/459.1 |
| 4,945,245 | 7/1990 | Levin | 250/458.1 |
| 5,032,730 | 7/1991 | Iwasaki | 250/458.1 |
| 5,061,857 | 10/1991 | Thompson et al. | 250/458.1 |
| 5,084,617 | 1/1992 | Gergely | 250/461.1 |
| 5,141,312 | 8/1992 | Thompson et al. | 356/218 |
| 5,221,957 | 6/1993 | Jannson et al. | 356/301 |
| 5,290,398 | 3/1994 | Feldman et al. | 156/651 |

OTHER PUBLICATIONS

Fiber-Optic Chemical Sensors for Competitive Binding Fluoroimmunoassay by Bruce J. Tromberg, et al, Anal. Chem. 1987, 59, pp. 1226–1230.
Fiber Optic-Based Immunosensors: A Progress Report, by S. K. Bhatia, et al, S.P.I.E. vol. 1054 (1989) pp. 184–190.
Component Selection for Fiber-Optic Fluorometry, by Richard B. Thompson, et al, Applied Spectroscopy, vol. 44, No. 1, 1990, pp. 117–122.
Fiber-Optic Fluorimetry in Biosensors: Comparison Between Evaanescent Wave Generation and Distal-Face Genration of Fluorescent Light, by A. Weber, et al, Biosensors & Bioelectronics 7 (1992), pp. 193–197.
Fiber Optic-based Biosensor: Signal Enhancement in a Production Model, by George P. Anderson, et al, Naval Research Lab, Center for Bio/Molecular Science and Engineering.

Primary Examiner—Robert P. Limanek
Assistant Examiner—David B. Hardy
Attorney, Agent, or Firm—Ann M. Kratz; Marvin Snyder

[57] ABSTRACT

An imaging system responsive to focused laser light includes a focusing lens for focusing the laser light and a mirror having a reflective side, a non-reflective side, and a hole for passing a predetermined portion of the laser light from the focusing lens through the non-reflective side. A fiber probe excites and couples fluorescence from an analyte. The fiber probe has a fiber front face for receiving laser light through the hole and for directing the fluorescence to the reflective side of the mirror. Optical devices for imaging the portion of the fluorescence reflected by the mirror to form an image of the fiber front face are provided, as well as an optical stop having an aperture in the image plane of the imaging means for reducing undesired light from the imaging means before reaching a detector. The mirror is angled for directing substantially all fluorescence from the the fiber probe into the imaging means rather than back toward the fiber probe.

26 Claims, 3 Drawing Sheets

OPTICAL SYSTEM FOR DETECTION OF SIGNAL IN FLUORESCENT IMMUNOASSAY

BACKGROUND OF THE INVENTION

1. Field of the Invention

This invention relates generally to the detection of analytes, and, more particularly, to a system for detecting levels of analytes measured with a laser induced fluorescence sensor (LIFS).

2. Description of the Related Art

In a fiber optic based LIFS probe, an energy field propagates through a fiber to an active region. In the active region, evanescent or distal field excitation leads to a fluorescent signal from an analyte outside the fiber. The fluorescent signal propagates back through the fiber and is used to estimate the concentration of the analyte. Typical uses for such probes include detecting hazardous waste and monitoring the contamination of a process stream.

A conventional optical system for a probe, as described in Thompson et al., U.S. Pat. No. 5,141,312, issued Aug. 25, 1992, includes a laser which provides excitation light through an angled dichroic mirror and then through an objective into a fiber. Fluorescence is directed back through the probe and objective towards the mirror and reflected into a detection lens and filter for focusing the fluorescence at a detection point.

A complementary system is described by Block et al., U.S. Pat. No. 4,582,809, issued Apr. 15, 1986. In this design the excitation light is reflected by a dichroic mirror through an objective into a fiber, while returning fluorescence is passed first through the objective, and then through the mirror into a photodetector.

The use of an objective between the mirror and probe causes stray reflections and fluorescences in the detection path. In the system described in aforementioned U.S. Pat. No. 5,141,312, a concave perforated mirror passes the laser excitation and focuses the returning signal fluorescence onto a detector, and a reflecting microscope objective is used as the objective to reduce photoluminescence originating in the objective. This technique has the limitation that the objective is present in the detection path and may create stray reflections and fluorescences which are transmitted to the detector, particularly if the reflecting objective is replaced by a standard glass microscope objective. Another problem with conventional systems is their need for precise alignment and positioning of each of the elements.

SUMMARY OF THE INVENTION

Accordingly, an object of the invention is to provide an imaging system for improved detection of a signal in fluorescent immunoassay.

Another object of the invention is to reduce stray reflections and fluorescences from the detection path of an optical system for a LIES probe.

Another object of the invention is to provide an imaging system which allows for precise relative alignment of the optics and the fiber optic probe.

Briefly, according to a preferred embodiment of the invention, an excitation system to deliver light to a fiber optic probe for exciting and coupling fluorescence from an analyte comprises a focusing lens for focusing excitation light and a mirror having a reflective side, a non-reflective side, and a hole for passing a predetermined portion of the converging excitation light from the focusing lens through the mirror. The fiber optic probe has a cleaved or polished fiber front face for receiving the focused excitation light through the hole and for directing the fluorescence to the reflective side of the mirror. An imaging means comprising a pair of achromatic lenses for collecting the portion of the fluorescence reflected by the mirror while simultaneously forming an image of the fiber front face is provided, as well as an optical stop having an aperture in the image plane of the imaging means for reducing undesired light from the imaging means before such light reaches a detector. The mirror is angled for directing substantially all fluorescence from the fiber probe into the imaging means rather than back toward the fiber probe.

One of the key features of this system is the avoidance of optical elements between the mirror and the fiber front face, which can reflect or scatter light into the detection optics. The complete separation of the excitation and detection optics eases the requirements of the position for an optional chopper. In conventional designs, the chopper needs to be placed close to the fiber between the focusing element and the fiber front face; otherwise, chopped light at the same wavelength as the analyte fluorescence can be generated in the focusing lens and misread by the detector as part of the signal. In the present invention, a chopper can be placed wherever convenient.

Both the hole in the mirror and the aperture in the optical stop act as spatial filters so that stray light is blocked from entering the detector.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings, where like numerals represent like components, in which:

DETAILED DESCRIPTION OF A PREFERRED EMBODIMENT OF THE INVENTION

Figure 1:
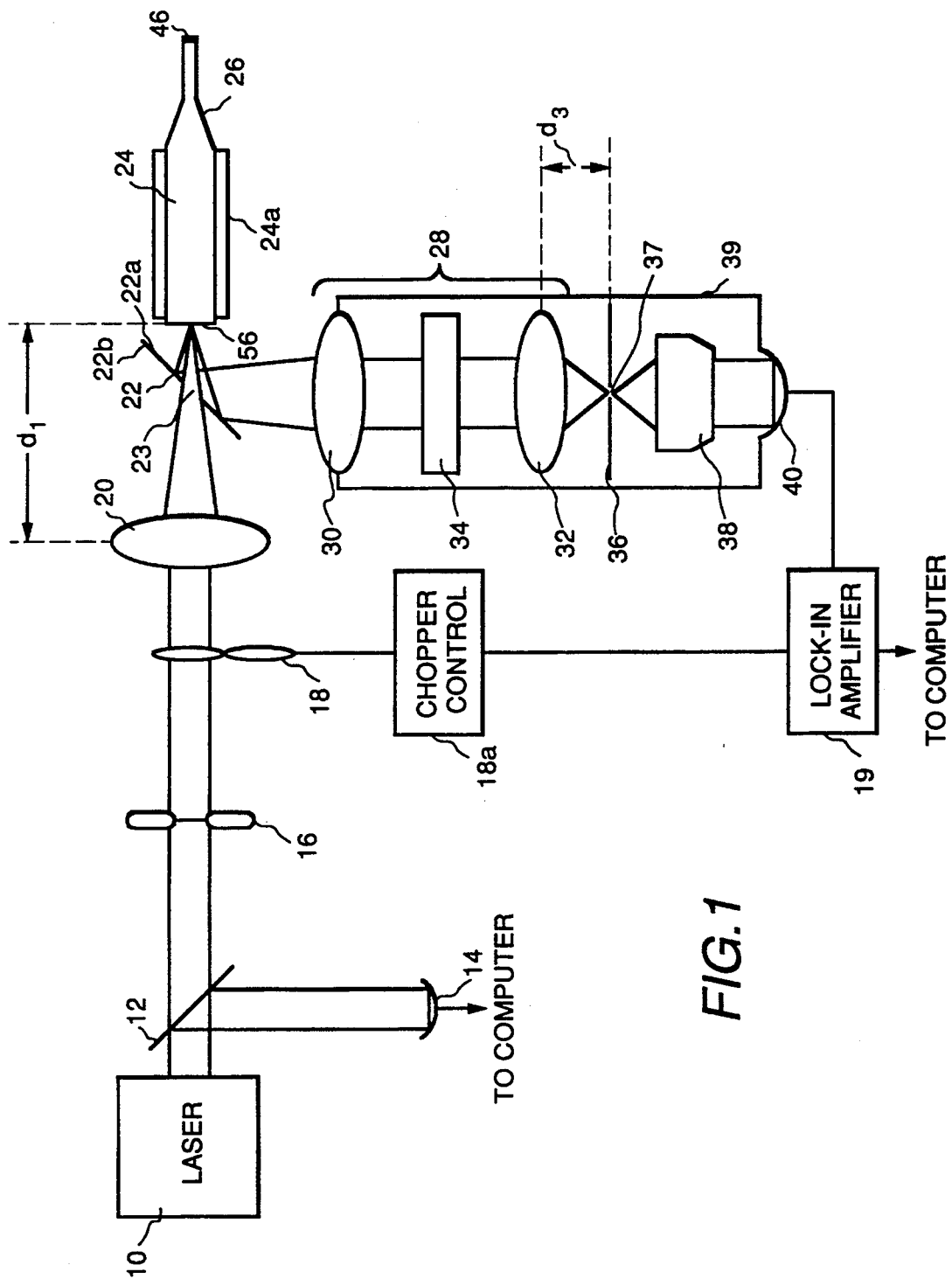
FIG. 1 is a schematic diagram of one embodiment of the optical system of the invention.

FIG. 1 is a schematic diagram of one embodiment of the optical system of the invention. A light source, shown as a laser 10, supplies excitation light for inducing fluorescence and may comprise, for example, either a continuous wave (CW) or pulsed laser. In a preferred embodiment, the light source comprises a CW argon laser with a wavelength of 488 nm. Other light sources can be used, for example, an arc lamp. Steering mirrors, used to position the optics more efficiently on a table, are not shown.

Preferably, a beam splitter 12 or glass/quartz fiat directs a predetermined amount of light to a power meter 14. These components are used because the signal from the analyte will vary with laser power, requiring the laser to be monitored during operation. Some lasers have built-in power meters.

An electronic shutter 16 is an optional feature of the invention which is used to limit the exposure of light to the fiber. Preferably the electronic shutter is a programmable shutter, such as made by Vincent Associates and sold under the name Uniblitz ® Electronic. The shutter is useful because the background signal drops with time when the fiber is exposed continuously to laser light. The shutter is not required if the measurement is made sufficiently quickly. By limiting the fiber exposure, the background becomes more constant. Typical exposure times are: 10 seconds per minute for a 10 minute period; 10 seconds per two minutes for a 20 minute period; and 10 seconds per 5 minutes for an indefinite period.

A chopper 18 is another optional feature of the invention which may be used with a CW laser. The chopper is used for improving the rejection of stray light from outside the system. In a preferred embodiment, chopper 18 is a rotating wheel chopper capable of chopping an excitation light at 10 Hz, such as those supplied by Stanford Research Systems, Inc., and controlled by a chopper control 18a. When a chopper (or a pulsed laser) is used, a lock-in-amplifier 19, such as model number 5210 supplied by EG&G Princeton Applied Research, is connected to the chopper control (or pulsed laser) and tuned to measure the output of a detector 40 only at the predetermined frequency of the chopper (or pulsed laser).

The present invention allows more design choices for placement of the chopper than conventional systems in that the chopper need not be placed directly in front of a fiber probe, and instead may be placed where convenient. In one embodiment, the preferred location of the chopper is between the shutter and a focusing lens 20.

Focusing lens 20 focuses light into fiber probe 24 through a hole 23 in a mirror 22. In a preferred embodiment wherein the light incident upon the focusing lens is collimated, the focusing lens is positioned so that it is separated from the fiber probe by a distance $d_1$ equalling the focusing lens focal length. In a preferred embodiment focusing lens 20 is a plane convex lens comprised of quartz.

Mirror 22, which is preferably planar as illustrated in FIG. 1, has a reflective side 22a, a non-reflective side 22b, and a hole 23 for passing a predetermined portion of laser light from focusing lens 20 through the mirror to fiber probe 24. The mirror is angled for directing substantially all fluorescence from the fiber probe into a system of imaging optics 28. The mirror typically comprises an aluminum coating on glass, and hole 23 has a diameter of approximately 1 mm. In a preferred embodiment, the mirror is situated at a 45 degree angle with respect to fiber probe 24.

In an embodiment in which a fiber probe is to be used to detect evanescently excited fluorescence, fiber probe 24 (shown with an exaggerated thickness) preferably comprises quartz and has a tapered fiber core 26 at the end opposite the fiber front face 56. A preferred method for tapering fibers and preferred fiber profiles are described in commonly assigned Feldman et al., "Synthesis of Tapers for Fiber Optic Sensors," U.S. Pat. No. 5,290,398, issued Mar. 1, 1994, which is herein incorporated by reference. Preferably the fiber is designed so that excess light transmitted through the probe is absorbed on a fiber back face 46 by, for example, black epoxy coated thereon. If the fiber is properly oriented, any laser light which is reflected from fiber front face 56 is directed back through the hole in the mirror and is not directed into imaging optics 28.

Imaging optics 28 preferably comprise a first imaging lens 30, a filter 34, and a second imaging lens 32. The first imaging lens is situated an optical distance $d_2$ which equals $d_{2a}$ plus $d_{2b}$ ($d_{2a}$ and $d_{2b}$ shown in FIG. 3) of one focal length away from the fiber. Preferably, the first and second imaging lenses are achromatic lenses which form a real, magnified image of the fiber front face that may be viewed using an optional eyepiece 38. Preferably, filter 34 is a holographic edge filter which eliminates laser light (of 488 nm wavelength) and stray light, and results in 70% transmission at a wavelength of 505 nm which is particularly appropriate for dyes customarily used as fluorescent labels, such as FITC (fluorescein isothiocyanate) dye. The filter is placed in the collimated beam between the two imaging lenses 30 and 32. In one preferred embodiment, for example, focusing lens 20 has a focal length of 100 mm, first imaging lens 30 has a focal length of 120 mm, second imaging lens 32 has a focal length of 50 mm, and fiber probe 24 is situated 37 mm from the midpoint of mirror 22.

Figure 4:
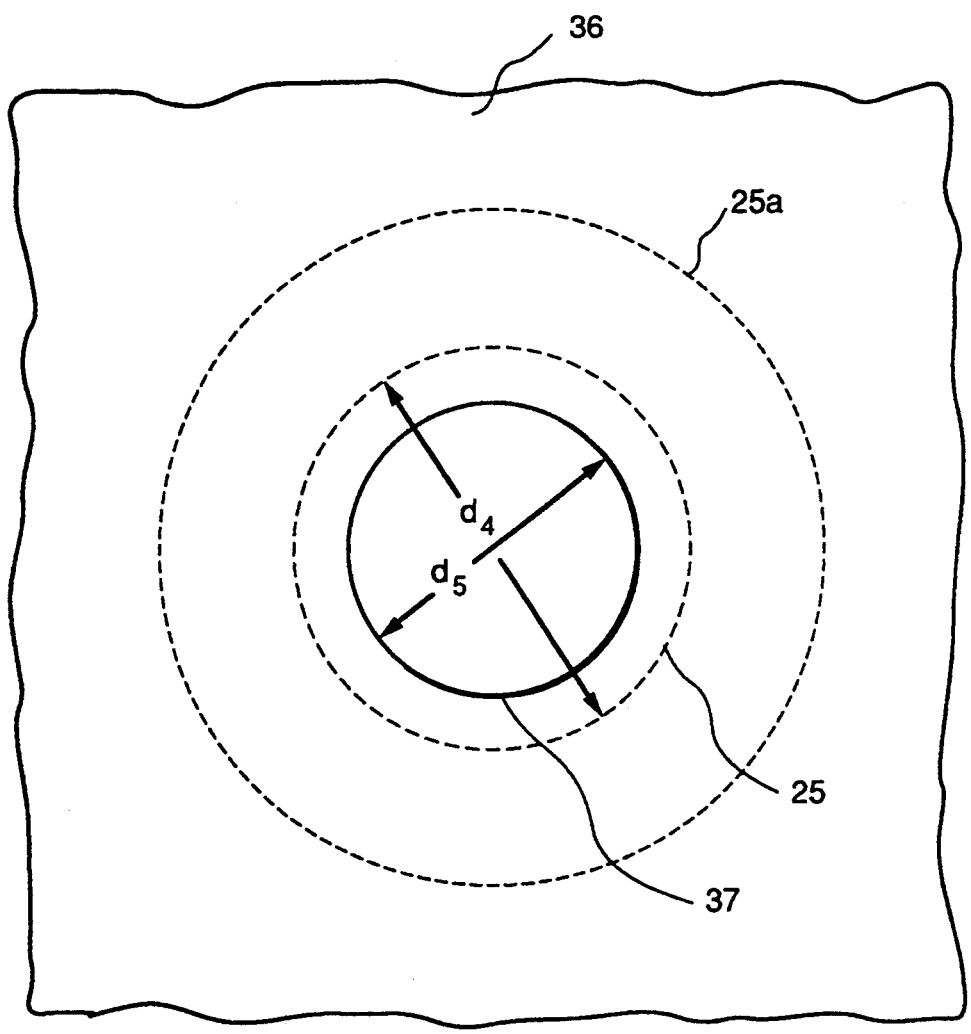
FIG. 4, is a view of an aperture in an image plane of the optical system of FIG. 1.

An optical step 36 having;an aperture 37 eliminates any remaining undesired or irrelevant light from the system, and thus improves the signal-to-noise ratio. The aperture is placed in the image plane of the system (at a distance $d_3$ of about one focal length of said second imaging lens away from said second imaging lens), and as shown in FIG. 4, preferably is slightly smaller than the diameter $d_4$ of the fiber core image 25 of the fiber front face at the image plane of the imaging means, in order to eliminate contributions from the fiber cladding 24a (which fluoresces more strongly than the fiber core and can cause an undesired fiber cladding image 25a). In one embodiment, the optical stop containing aperture 37 comprises an aluminum sheet coated with highly absorbing black epoxy to eliminate stray reflections. In another embodiment, the optical stop comprises a black anodized aluminum sheet.

Optional eyepiece 38, Such as a 20 mm focal length Erfle eyepiece supplied by Edmund Scientific Company, can be used to magnify the image for easier alignment. If no eyepiece is used, detector 40 can be placed at the image plane, just behind aperture 37.

Preferably, the entire imaging system, including the first and second imaging lenses 30 and 32, filter 34, optical stop 36 and, if applicable, eyepiece 38, is enclosed in an anodized aluminum tube 39 to reduce stray light.

Detector 40 preferably comprises a photodiode, such as supplied by Haruamatsu Corporation, with a high gain feedback circuit. The detector can be placed behind optional eyepiece 38 and connected to optional lock-in amplifier 19 (used with pulsed laser light or chopped CW laser light) and a computer (not shown). When detector 40 is removed, fiber front face 56 may be viewed through eyepiece 38 and imaging lenses 30 and 32.

Optical alignment of the system begins by sending a laser beam through focusing lens 20 and positioning mirror 22 so that nearly all the light is passed through hole 23 in the mirror. Then a polished fiber 24 is positioned for maximum throughput of laser light and so the laser light reflected from the fiber front face 56 is passed back through hole 23. Preferably a piece of test fiber polished on both ends is used, so that light may be sent through the fiber from its fiber back face 46 and reflected into the imaging systems. Imaging lenses 30 and 32 and filter 34 are positioned to form a real image of fiber front face 56 and to block any additional scattered excitation light which is not directed through hole 23 in the mirror 22. This can be done either by directing light from fiber back face 46 through the fiber or by reflecting light from the fiber back face. Eyepiece 38 is next positioned for viewing the image, and optical stop 36 is inserted so that aperture 37 therein appears concentric with fiber front face 56.

When the lenses and aperture are properly aligned with respect to the fiber in this manner, changing the fiber requires that the user simply look through eyepiece 38 and position the fiber so that fiber front face 56 is in focus and correctly aligned with aperture 37. Detector 40 can be positioned by directing light through the fiber from the fiber back face and adjusting the detector location until it is at the focal point of the eyepiece. Detector 40 can be securely bolted to a high quality kinematic mount (not shown), such as supplied by ThorLabs Inc., so that the detector may be repeatedly removed and replaced without significant variation in position.

Figure 2A:
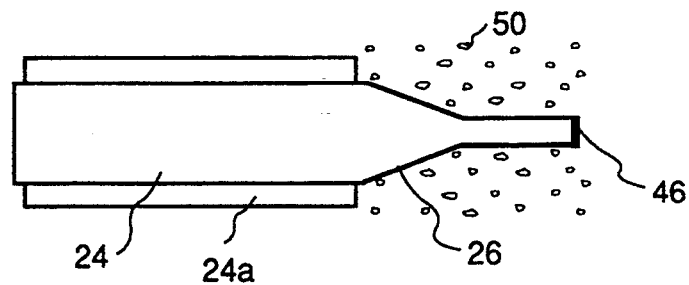
FIGS. 2(a)–2(b) are views of alternative types of fiber probes which can be used in the system shown in FIG. 1.
Figure 2B:
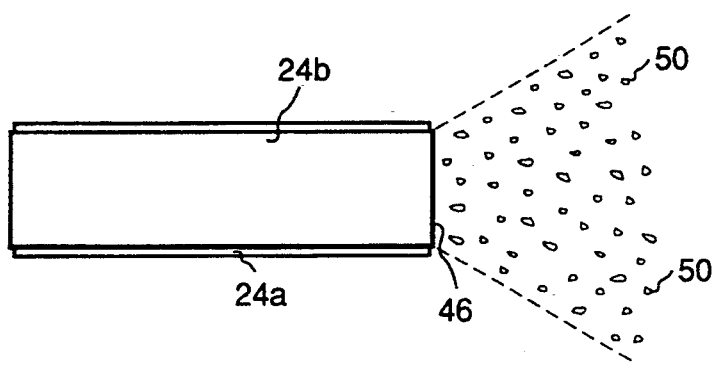

FIGS. 2(a)-2(b) are views of alternative types of fiber probes which can be used in the system shown in FIG. 1. FIG. 2(a) illustrates the preferred embodiment wherein fiber probe 24 is an evanescent field fiber optic based laser induced fluorescence sensor (LIFS) probe. In response to excitation light, analytes 50 fluoresce, and a fluorescent signal propagates back through fiber 24. In the embodiment of FIG. 2(a) the fluorescence is measured along the sides of fiber probe 24 (which in this case include tapered portion 26).

FIG. 2(b) illustrates a LIFS probe embodiment for observing direct field fluorescence from the fiber back face 46 of a fiber optic probe 24b. In this case, the fiber back face, which is polished or cleaved and has no absorbent material coated thereon, is the surface at which fluorescence from analytes 50 enters probe 24b.

Figure 3:
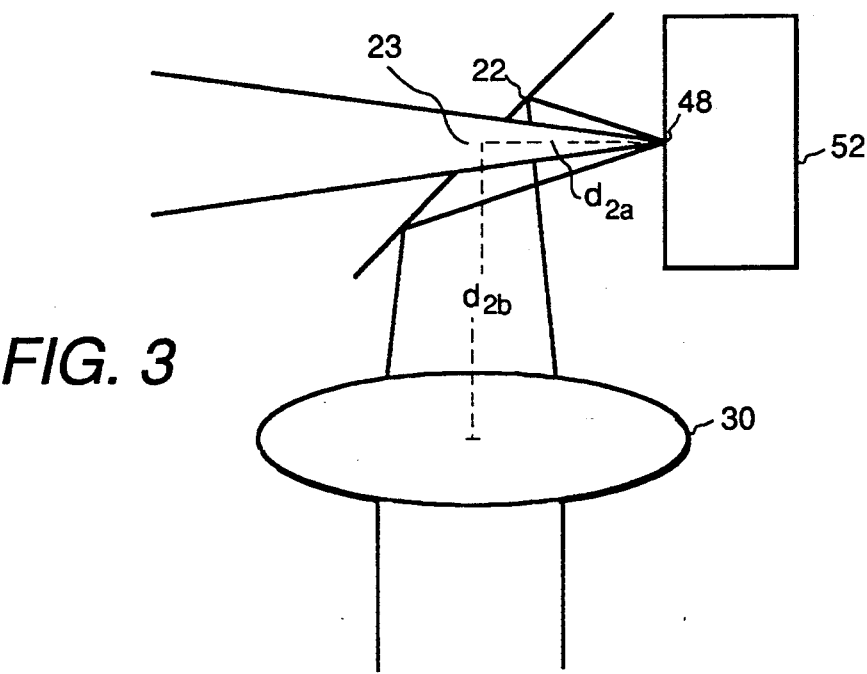
FIG. 3 is a partial view of an alternative embodiment of the present invention in which a fiber probe is not required.

FIG. 3 is a partial view of an alternative embodiment of the present invention in which a fiber probe is not required. A signal may be detected in a small region 48 of any surface 52 or bulk medium by situating region 48 in the focal plane of imaging lens 20. Surface 52 may comprise, for example, contaminated concrete, and an example of a bulk medium is ocean water. Each of the other elements of the invention discussed with respect to FIG. 1 operates in a similar manner when a fiber probe is replaced with surface 52—the only distinctions are that the detected region is smaller and the angle of fluorescence directed to mirror 22 is wider.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An optical system for delivering excitation light to a chemical sensor and receiving an optical signal from the sensor, comprising:
   a focusing lens for focusing said excitation light;
   a planar mirror having a reflective side, a non-reflective side, and a hole for passing a predetermined portion of said excitation light from said focusing lens through said mirror;
   a region for exciting and coupling fluorescence from an analyte, said region capable of receiving excitation light through said hole and of directing said fluorescence to said reflective side of said mirror;
   imaging means for optically imaging the portion of said fluorescence reflected by said mirror to form an image of said region, said imaging means having an image plane;
   an optical stop having a substantially circular aperture in the image plane of said imaging means for blocking undesired light from said imaging means and passing desired light from said imaging means; and
   a detector situated in a path of said desired light emerging from said aperture in said optical stop;
   said mirror being angled for directing substantially all fluorescence from said region into said imaging means.

2. The system of claim 1, wherein said region is one selected from a group consisting of a surface medium and a bulk medium.

3. The system of claim 1, wherein said region comprises a fiber probe including a fiber front face, a fiber back face, a fiber core, and a fiber cladding.

4. The system of claim 3, further including a shutter situated to limit the excitation light that reaches said focusing lens.

5. The system of claim 4, wherein said shutter comprises a programmable electronic shutter.

6. The system of claim 3, further including a continuous wave laser for supplying said excitation light and a chopper situated to chop said excitation light at a desired frequency.

7. The system of claim 6, further including a lock-in amplifier coupled to said detector for measuring an output signal of said detector at said desired frequency.

8. The system of claim 6, wherein said chopper comprises a rotating wheel chopper positioned between said focusing lens and said laser.

9. The system of claim 3, further including means disposed on said fiber back face for absorbing light transmitted through said probe.

10. The system of claim 9, wherein said absorbing means comprises dark epoxy.

11. The system of claim 9, wherein said fiber probe includes a tapered fiber core.

12. The system of claim 3, wherein said fiber back face is one selected from a group consisting of polished fiber faces and cleaved fiber faces.

13. The system of claim 3, wherein said imaging means comprises:
   a first imaging lens and a second imaging lens for imaging said fluorescence; and
   a filter positioned between said first and second lenses for blocking stray light.

14. The system of claim 13, wherein said filter comprises a holographic edge filter.

15. The system of claim 13, wherein:
   said focusing lens is situated at a first distance of approximately one focal length of said focusing lens away from said fiber front face,
   said first imaging lens is situated at an optical distance of approximately one focal length of said first imaging lens away from said fiber front face, and
   said second imaging lens is situated at a second distance of approximately one focal length of said second imaging lens away from said optical stop having said aperture.

16. The system of claim 3, wherein said aperture has a diameter smaller than a diameter of a fiber core image of said fiber front face in the image plane of said imaging means.

17. The system of claim 3, further including an eyepiece for magnifying said image of said fiber front face, said eyepiece situated between said aperture and said detecter.

18. The system of claim 3, wherein said detector comprises a photodiode.

19. The system of claim 18, further including an amplifying circuit coupled to said photodiode.

20. The system of claim 3, further including a pulsed laser for providing said excitation light.

21. The system of claim 3, wherein said aperture has a diameter sized to minimize contribution of background light from said fiber cladding.

22. A method for detecting analytes in a test region, comprising:
   inserting a fiber optic probe into the test region;
   directing energy onto a front face of said probe so as to excite fluorescence in said analytes, such that said fluorescence illuminates said fiber optic probe;
   coupling said fluorescence produced by said analytes out of said probe through said front face onto a reflecting surface;
   optically imaging said fluorescence reflected by said reflecting surface to form an image of said front face on an image plane; and
   positioning an aperture at said image plane to pass a portion of said fluorescence to an optical detector.

23. The method of claim 22, wherein said reflecting surface is situated astride the path of said energy and located in a position such that said energy passes said position essentially undiminished.

24. The method of claim 23, wherein said reflecting surface includes a hole.

25. The method of claim 22, wherein directing said energy onto said front face comprises focusing said energy onto said front face.

26. The method of claim 22, further including imaging said fluorescence through said aperture after coupling said fluorescence onto said reflecting surface.

* * * * *